United States Patent [19]
Lehnert et al.

[11] Patent Number: 6,063,959
[45] Date of Patent: May 16, 2000

[54] PURIFICATION OF CRUDE ACRYLIC ACID BY CRYSTALLIZATION

[75] Inventors: Klaus Lehnert, Mutterstadt; Klaus Joachim Müller-Engel, Stutensee; Gerhard Nestler, Ludwigshafen; Bernd Eck, Vierheim, all of Germany

[73] Assignee: BASF Aktiengesellschaft, Ludwigshafen, Germany

[21] Appl. No.: 09/147,457

[22] PCT Filed: Jun. 24, 1997

[86] PCT No.: PCT/EP97/03304

§ 371 Date: Dec. 30, 1998

§ 102(e) Date: Dec. 30, 1998

[87] PCT Pub. No.: WO98/01414

PCT Pub. Date: Jan. 15, 1998

[30] Foreign Application Priority Data

Jul. 10, 1996 [DE] Germany ............................. 196 27 679

[51] Int. Cl.$^7$ ........................................................ C07C 51/43
[52] U.S. Cl. .............................................. 562/600; 562/598
[58] Field of Search ....................................... 562/600, 598

[56] References Cited

FOREIGN PATENT DOCUMENTS

| 0 297 445 | 6/1988 | European Pat. Off. . |
| 0 616 998 | 3/1994 | European Pat. Off. . |
| 2 136 396 | 7/1971 | Germany . |

*Primary Examiner*—Rosalynd Keys
*Attorney, Agent, or Firm*—Oblon, Spivak, McClelland, Maier & Neustadt, P.C.

[57] ABSTRACT

1,4-Dibenzothiazine-comprising crude acrylic acid is purified by crystallization by raising its diacrylic acid content to at least 1% by weight prior to the crystallization step.

13 Claims, No Drawings

PURIFICATION OF CRUDE ACRYLIC ACID BY CRYSTALLIZATION

The present invention relates to a process for purifying crude acrylic acid by crystallization.

Acrylic acid, whether as acid or in the form of its salts or esters, is particularly important for preparing polymers for a very wide range of application areas, for example adhesives, superabsorbents, binders.

One way of obtaining acrylic acid is by catalytic gas phase oxidation of propane, propene and/or acrolein. In the catalytic gas phase oxidation process, these starting gases are diluted, generally with inert gases such as nitrogen, $CO_2$ and/or steam, and passed together with oxygen over transition metal mixed-oxide catalysts at elevated temperatures and, if necessary, elevated pressure for oxidative conversion into a mixture of products which includes acrylic acid. By condensing the product mixture or by absorption into a suitable absorbent (e.g. water or a mixture of 70–75% by weight of diphenyl ether and 25–30% by weight of biphenyl), it is possible to achieve a basic separation of the acrylic acid from the product gas stream (cf. for example EP-A 297 445 and DE-C-21 36 396).

Removal of the absorbent (following, if necessary, prior desorption of impurities having a low absorbent solubility, by stripping, for example with air) by extractive and/or distillative methods of separation (e.g. removal of the aqueous absorbent by distillation, azeotropic distillation or extractive separation of the acid from the aqueous solution and subsequent distillative removal of the extractant) and/or following application of other separating steps frequently yields an acrylic acid which is herein referred to as a crude acrylic acid.

This crude acrylic acid is not a pure product. On the contrary, it comprises a spectrum of different impurities typical of production by oxidative gas phase catalysis. These impurities are in particular acetic acid, propionic acid, water and low molecular weight aldehydes such as acrolein, methacrolein, propionaldehyde, n-butyraldehyde, benzaldehyde, furfurals and crotonaldehyde.

Crude acrylic acid further typically comprises polymerization inhibitors. These are added in the course of the separation processes employed for producing crude acrylic acid for the purposes of suppressing any free-radical polymerization of the α, β-monoethylenically unsaturated acrylic acid, which is why they are also known as process stabilizers. The preeminent acrylic acid process stabilizer is 1,4-dibenzothiazine,

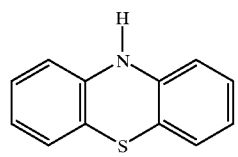

1,4-Dibenzothiazine is a colorless substance with a melting point of 180° C. (at 1 bar), which is obtainable by heating diphenylamine with sulfur. 1,4-Dibenzothiazine is typically used as sole acrylic acid process stabilizer or in combination with other possible acrylic acid process stabilizers, for example hydroquinone, which is why 1,4-dibenzothiazine is a characteristic constituent of the crude acrylic acid relevant herein.

Further undesirable concomitants of condensed-phase acrylic acid are the acrylic acid oligomers formed by Michael addition of acrylic acid to itself and to the resulting acrylic acid dimer. Whereas these Michael adducts are normally hardly present in freshly produced crude acrylic acid (their weight proportion being typically <0.01% by weight), they form therein on prolonged standing. Statistically, merely the formation of diacrylic acid

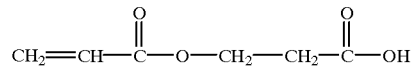

is important, whereas the formation of higher acrylic acid oligomers (trimers, tetramers, etc.) is essentially negligible.

In fact, even the formation of diacrylic acid is a slow process. A ≧99.5% by weight pure acrylic acid left to stand at 25° C. and 1 bar will generate about 150 weight ppm of diacrylic acid per day, based on acrylic acid. The total amount of any other cocomponents present in the crude acrylic acid is generally not more than 10% by weight, based on the weight of the crude acrylic acid.

Crude acrylic acid for the purposes of this invention is therefore an acrylic acid comprising, if its acrylic acid oligomer[1] (Michael adducts) content is ignored, ≧70% by weight of acrylic acid,
≦20% by weight of acetic acid,
≦5% by weight of propionic acid,
≦5% by weight of water,
≦5% by weight of low molecular weight aldehydes, and
≧0.80% by weight of 1,4-dibenzothiazine;

that is, the weight %ages are based on the weight of the crude acrylic acid minus its acrylic acid oligomer content.

[1] Acrylic acid oligomers are herein always to be understood as meaning the corresponding Michael adducts and not acrylic acid oligomers formed by free-radical polymerization, since the formation of the latter is essentially suppressed by the presence of polymerization inhibitors.

More particularly, crude acrylic acid shall herein be understood as meaning an acrylic acid comprising, if its acrylic acid oligomer content is ignored, ≧80% by weight of acrylic acid,
≦15% by weight of acetic acid,
≦5% by weight of propionic acid,
≦5% by weight of water,
≦5% by weight of low molecular weight aldehydes and
≧0.80% by weight of 1,4-dibenzothiazine.

Accordingly, the term "crude acrylic acid" as used herein will also encompass an acrylic acid comprising, if its acrylic acid oligomer content is ignored, ≧90% by weight of acrylic acid,
≦5% by weight of acetic acid,
≦2% by weight of propionic acid,
≦2% by weight of water,
≦2% by weight of low molecular weight aldehydes and
≧0.80% by weight of 1,4-dibenzothiazine.

Most of the constituents present in the aforementioned crude acrylic acids alongside acrylic acid are disadvantageous for the use of the acrylic acid.

If such a crude acrylic acid were used for example for preparing acrylic esters with $C_1$–$C_8$-alkanols, the corresponding acetic and propionic esters would be formed in secondary reactions, which would reduce the yield of the desired acrylic ester, based on the amount of alkanol used. If the acrylic esters formed in the presence of the low molecular weight aldehydes are used in free-radical polymerizations, the presence of the low molecular weight aldehydes generally has an adverse effect for example in that they affect the induction time of polymerization reactions, i.e. the period between the attainment of the polymerization temperature and the actual start of the polymerization. They further generally affect the degree of polymerization and may also cause discolorations in the polymers.

The aforementioned disadvantages normally even apply when the crude acrylic acid is used directly as a source of acrylic acid in polymerizations.

It is therefore incumbent upon acrylic acid producers to remove the impurities present in crude acrylic acid as far as possible.

Two grades of purity are typically commercially available:
  pure acrylic acid, having a purity of at least 99% by weight, based on the sum of all constituents, frequently even ≧99.5% by weight;
  esterification-grade acrylic acid, having a purity of at least 98% by weight, based on the sum of all constituents, frequently even ≧99% by weight.

Pure acrylic acid is used in particular for making superabsorbents (=materials for absorbing water which are based on polyacrylic acid and salts thereof) and in this respect is subject in particular to the requirement of ideally not comprising any diacrylic acid or any 1,4-dibenzothiazine, since these two compounds are undesirable either in superabsorbent-making (1,4-dibenzothiazine in particular interferes greatly with the making of superabsorbents owing to its extremely inhibiting effect on free-radical polymerizations) or in superabsorbent use (superabsorbents are used in particular in the hygiene sector (e.g. baby's diapers); the presence of uncopolymerized diacrylic acid (which polymerizes to a less marked extent than acrylic acid) is not tolerable in this application sector). The storage stabilization of pure acrylic acid against undesirable premature free-radical polymerization is therefore customarily effected by means of hydroquinone monomethyl ether or monoethyl ether or mixtures thereof. These compounds have a comparatively less inhibiting effect, which is appropriate to the comparatively low stress profile of storage.

Pure acrylic acid is therefore normally produced by direct further processing of freshly produced crude acrylic acid, since the latter is at that stage virtually free of any acrylic acid oligomer. Pure acrylic acid is customarily used in the freshly prepared state.

Furthermore, purification is advantageously effected using fractional crystallization as described for example in EP-A 616 998, since said fractional crystallization is carried out at low temperatures (according to Louis F. Fieser and Mary Fieser, Organische Chemie, Verlag Chemie (1975), p. 422, Table 11.1., the melting point of pure acrylic acid is 13° C. at 1 bar; the presence of foreign components further lowers the crystallization temperature) and low temperatures additionally inhibit both the Michael addition and the free-radical polymerization of acrylic acid.

However, the disadvantage of purifying crude acrylic acid by crystallization is the low solubility of 1,4-dibenzothiazine in acrylic acid, which is about 1.5% by weight at 25° C. and only about 0.9% by weight at 15° C., based on the solution of acrylic acid and 1,4-dibenzothiazine. The presence of acetic acid and/or propionic acid in acrylic acid has hardly any effect on these solubility values, whereas the presence of water further reduces the solubility of 1,4-dibenzothiazine. This has essentially the following consequences:

On cooling a crude acrylic acid whose 1,4-dibenzothiazine content is above the level of the eutectic mixture with acrylic acid, the 1,4-dibenzothiazine will precipitate first, not the acrylic acid. In other words, pure acrylic acid cannot be separated off. Cooling a crude acrylic acid whose 1,4-dibenzothiazine content is below the level of the eutectic mixture with acrylic acid will, it is true, first bring down pure acrylic acid, which can be separated off as such. However, such removal of pure acrylic acid is accompanied by an increase in the concentration of the 1,4-dibenzothiazine remaining in the melt until the eutectic composition is reached, and it is no longer pure acrylic acid but the eutectic mixture of 1,4-dibenzothiazine and acrylic acid which will precipitate.

The lower the solubility of a compound in acrylic acid at a certain temperature, normally the lower its weight proportion in the eutectic mixture. If, then, the eutectic composition is reached at a very low level of 1,4-dibenzothiazine, fractional crystallization will not achieve any further removal of pure acrylic acid. On the contrary, the eutectic mixture will represent an unsellable waste. Here the only remedies to date have been auxiliary measures such as melting the eutectic mixture and then selectively precipitating its 1,4-dibenzothiazine content by addition of selective precipitants, for example water, or by application of special crystallization processes in which the crystallization surfaces are for example seeded with crystals of one of the constituents of the eutectic mixture.

It is an object of the present invention to find a suitable measure to raise the solubility of 1,4-dibenzothiazine in acrylic acid, thereby to raise the proportion of 1,4-dibenzothiazine in the corresponding eutectic mixture and so provide an improved process for purifying crude acrylic acid by crystallization.

We have found that this object is achieved by a process for purifying crude acrylic acid by crystallization which comprises adjusting the diacrylic acid content of the crude acrylic acid to a value of at least 1% by weight, based on the total weight of the crude acrylic acid, prior to the crystallization step, since, surprisingly, the solubility of 1,4-dibenzothiazine in acrylic acid can be increased by more than 100%, especially at the crystallization-relevant temperatures, with an increasing level in the acrylic acid of diacrylic acid (Michael adduct of acrylic acid with itself).

Processes according to this invention are accordingly those processes for purifying crude acrylic acid whose diacrylic acid content is adjusted to a value of from 1 to 2% by weight, or from 1 to 3% by weight, or from 1 to 5% by weight, or from 1 to 10% by weight, or from 1 to 20% by weight, or from 1 to 40% by weight, on the above basis, prior to the crystallization step. According to this invention, it is generally not advantageous for the crude acrylic acid to be purified by crystallization to have a diacrylic acid content of above 50% by weight.

The process of this invention is thus naturally suitable for crude acrylic acid whose 1,4-dibenzothiazine content, based on the weight of crude acrylic acid minus the amount of acrylic acid oligomers it contains, is ≧0.9% by weight, or ≧1% by weight, or ≧1.1% by weight, or ≧1.2% by weight, or ≧1.3% by weight, or ≧1.4% by weight, or ≧1.5% by weight. Normally, the 1,4-dibenzothiazine content on that basis will be not more than 2% by weight. The process of this invention can also be used when the crude acrylic acid comprises hydroquinone in amounts of up to 5% by weight.

An advantage for the process of this invention is that diacrylic acid has an increased solubility in acrylic acid itself. It is further advantageous that diacrylic acid can be cleaved back to acrylic acid by application of elevated temperature.

The adjustment required for the purposes of this invention in the diacrylic acid content of the crude acrylic acid to be purified by crystallization can be realized in various ways. One possibility is to add to the crude acrylic acid to be purified a small amount of a strong protic mineral acid, for example $H_2SO_4$, HCl or $H_3PO_4$, which catalyzes the Michael addition of acrylic acid. The presence of $H_2O$ likewise favors the formation of diacrylic acid. After sufficient diacrylic acid formation, which if necessary can be additionally augmented by means of a moderate increase in the temperature, the catalytic effect of the mineral acid can be eliminated again by adding a neutralizing base. Of course, the diacrylic acid content can also be increased by removing some of the other constituents present, for example by distillation and/or crystallization, in first separating steps.

Alternatively, diacrylic acid can be grown in pure acrylic acid, separated off, for example by distillation, and added to the crude acrylic acid to be purified by crystallization.

It will be appreciated that the process of this invention is normally carried out at atmospheric pressure, i.e. at a pressure of 1 bar.

The process of this invention will be typically realized as a fractional crystallization. The individual crystallization stages can be realized both as static and/or as dynamic crystallization. Both layer crystallization such as falling-film crystallization and suspension crystallization can be used. An extensive description of these crystallization techniques is given in EP-A 616 998 and the references cited therein.

The advantages of the process of this invention can be utilized in the course of a cleverly coupled production of esterification-grade acrylic acid and pure acrylic acid not only with a crude acrylic acid which meets the definition of the present invention, but also with a crude acrylic acid comprising an amount of 1,4-dibenzothiazine which differs from 0, but is below the 0.8% by weight limit of this invention.

First, esterification-grade acrylic acid is continuously produced in first crystallization and/or distillation steps. Since the esterification-grade acrylic acid has to be process-stabilized for the esterification, its 1,4-dibenzothiazine content does not have an adverse effect (for esterification-grade acrylic acid, the upper limit to be observed for the 1,4-dibenzothiazine content is 750 weight ppm and the corresponding limit for diacrylic acid is 1.5%; for pure acrylic acid, the upper limit to be observed for the 1,4-dibenzothiazine content is 1 ppm and the corresponding diacrylic acid limit is 0.2% by weight if used for customary polymerizations and 500 ppm if used for making superabsorbents).

The resulting esterification-grade, 1,4-dibenzothiazine-comprising acrylic acid is then at least partly intermediately stored for a few days, a week, a month, three months, six months or longer. This intermediate store of acrylic acid can then be used as required for producing acrylic esters or for preparing pure acrylic acid by crystallization. Formation of diacrylic acid in the course of intermediate storage, something which is customarily sought to be prevented if pure acrylic acid is to be produced, is barely noticeable in the esterification, since a back-cleavage employed in the course of the workup of the esterification mixture will ultimately prevent yield losses, based on alkanol used. As outlined herein, however, the diacrylic acid formed in the course of storage has an advantageous effect on the crystallizational further purification of esterification-grade acrylic acid for preparing pure acrylic acid which is substantially free of 1,4-dibenzothiazine.

Table 1 below shows the increase in the solubility of 1,4-dibenzothiazine in acrylic acid with increasing diacrylic acid content for two temperatures as a result of solubility trials.

TABLE 1

| | Solubility of 1,4-dibenzothiazine (in % by weight, based on acid) | |
|---|---|---|
| Composition of acid | 15° C. | 25° C. |
| 100% by weight of acrylic acid | 0.9% by weight | 1.5% by weight |
| 97% by weight of acrylic acid 3% by weight of diacrylic acid | 1.45% by weight | 2.10% by weight |
| 95% by weight of acrylic acid 5% by weight of diacrylic acid | 1.71% by weight | 2.15% by weight |
| 90% by weight of acrylic acid 10% by weight of diacrylic acid | 1.83% by weight | 2.25% by weight |
| 80% by weight of acrylic acid 20% by weight of diacrylic acid | 2.01% by weight | 2.51% by weight |
| 73% by weight of acrylic acid 27% by weight of diacrylic acid | | 2.60% by weight |
| 55% by weight of acrylic acid 45% by weight of diacrylic acid | | 2.90% by weight |
| 10% by weight of acrylic acid 90% by weight of diacrylic acid | | 3.20% by weight |

Table 2 below shows the solubility of 1,4-dibenzothiazine in acetic acid.

TABLE 2

| Temperature (°C.) | Solubility (% by weight, based on solution) |
|---|---|
| 5 | 0.28 |
| 10 | 0.89 |
| 20 | 1.25 |
| 30 | 1.53 |

We claim:

1. A process for purifing, by crystallization, a crude acrylic acid having the following composition while disregarding the acrylic acid oligomer content of the crude acrylic acid:

≧70% by weight of acrylic acid,
≦20% by weight of acetic acid,
≦5% by weight of propionic acid,
≦5% by weight of water,
≦5% by weight of low molecular weight aldehydes, and
≧0.80% by weight of 1,4-dibenzothiazine;

which comprises:

adjusting the diacrylic acid content of the crude acrylic acid to a value of at least 1% by weight, based on the total weight of the crude acrylic acid including the acrylic acid oligomer content of the crude acid, prior to crystallizing the crude acrylic acid.

2. The process as claimed in claim 1, wherein the diacrylic acid content of the crude acrylic acid is adjusted to at least 5% by weight, based on the total weight of the crude acrylic acid.

3. The process as claimed in claim 1, wherein the crude acrylic acid to be crystallized comprises $\geq 0.9\%$ by weight of 1,4-dibenzothiazine, disregarding the acrylic acid oligomer content of the crude acid.

4. The process as claimed in claim 2, wherein the crude acrylic acid to be crystallized comprises $\geq 0.9\%$ by weight of 1,4-dibenzothiazine, disregarding the acrylic acid oligomer content of the crude acid.

5. The process as claimed in claim 3, wherein said 1,4-dibenzothiazine content of the crude acrylic acid is $\geq 1.0\%$ by weight.

6. The process as claimed in claim 4 wherein said 1,4-dibenzothiazine content of said crude acrylic acid is $\geq 1.1\%$ by weight.

7. The process as claimed in claim 5, wherein said 1,4-dibenzothiazine content of said crude acrylic acid is $\geq 1.1\%$ by weight.

8. The process as claimed in claim 7, wherein said 1,4-dibenzothiazine content of said crude acrylic acid is $\geq 1.2\%$ by weight.

9. The process as claimed in claim 6, wherein said 1,4-dibenzothiazine content of said crude acrylic acid is $\geq 1.2\%$ by weight.

10. The process as claimed in claim 8, wherein said 1,4-dibenzothiazine content of said crude acrylic acid is $\geq 1.3\%$ by weight.

11. The process as claimed in claim 9, wherein said 1,4-dibenzothiazine content of said crude acrylic acid is $\geq 1.3\%$ by weight.

12. The process as claimed in claim 10, wherein the diacrylic acid content of the crude acrylic acid, upon adjustment, is not above 50% by weight of the crude acrylic acid based on the total weight of the crude acid containing oligomers of acrylic acid.

13. The process as claimed in claim 11, wherein the diacrylic acid content of the crude acrylic acid, upon adjustment, is not above 50% by weight of the crude acrylic acid based on the total weight of the crude acid containing oligomers of acrylic acid.

* * * * *